United States Patent
Davis et al.

(10) Patent No.: US 7,033,836 B1
(45) Date of Patent: Apr. 25, 2006

(54) MASTITIS DETECTION METHOD

(75) Inventors: Stephen Davis, Hamilton (NZ); Colin George Prosser, Matangi (NZ); Gina Diane Nicholas, Hamilton (NZ); Julian Lee, Palmerston, North (NZ); Alan Leedham Hart, Palmerston, North (NZ); Vicki Clare Farr, Matangi (NZ)

(73) Assignee: New Zealand Pastoral Agricultural Research Institute, Hamilton (NZ)

(*) Notice: Subject to any disclaimer, the term of this patent is extended or adjusted under 35 U.S.C. 154(b) by 681 days.

(21) Appl. No.: 09/979,981

(22) PCT Filed: Jun. 9, 2000

(86) PCT No.: PCT/NZ00/00096

§ 371 (c)(1),
(2), (4) Date: Mar. 4, 2002

(87) PCT Pub. No.: WO00/75654

PCT Pub. Date: Dec. 14, 2000

(30) Foreign Application Priority Data

Jun. 9, 1999 (NZ) .................... 336089

(51) Int. Cl.
*G01N 33/00* (2006.01)

(52) U.S. Cl. .................... 436/20; 436/23; 436/811
(58) Field of Classification Search ............. 436/20, 436/23, 811
See application file for complete search history.

(56) References Cited

U.S. PATENT DOCUMENTS

| | | | |
|---|---|---|---|
| 4,830,011 A | 5/1989 | Lim | |
| 5,743,209 A | 4/1998 | Bazin | |
| 6,814,025 B1 * | 11/2004 | Chen et al. ............ | 119/14.01 |

FOREIGN PATENT DOCUMENTS

| | | |
|---|---|---|
| EP | 0472295 | 2/1992 |
| EP | 0534564 | 3/1993 |
| EP | 0 628 244 A1 | 12/1994 |
| SU | 1582389 A1 * | 6/1996 |
| WO | 95 20159 | 7/1995 |

OTHER PUBLICATIONS

Hamann et al.:Livestock Production Science 48(1997) 201-208; Potential of Specific Milk Composition Variables for Cow Health Management.

Nogai et al. Die Beeinflussung von Pyrovat und L(+)—Lactat in Milch; Institut Fur Hygiene und Technologie der Milch pp37-42 Oct. 7, 2004.

Dictionary of Agriculture, second edition, Peter Collins Publishing, 1996, pp 158/159.

Jobst et al.; Application of Miniaturized Liquid Handling Biosensor Array for Milk Analysis; Transducers '95-Eurosensors X pp 473-474.

(Continued)

*Primary Examiner*—Monique T. Cole
(74) *Attorney, Agent, or Firm*—Lowe Hauptman & Berner, LLP

(57) ABSTRACT

The invention relates to a method for detecting mastitis in an animal, characterized by the steps of collecting milk from the animal, and assaying the milk for a substance produced in the animal in an anaerobic environment, and comparing the substance levels obtained with typical substance levels found in uninfected milk.

12 Claims, 3 Drawing Sheets

OTHER PUBLICATIONS

Walstra et al.; Dairy technology, Principals of Milk Properties and Processing; pp 98-99.

Pitkin et al.; The Possible Significance of Lactic Acid levels in Normal and Abnormal Milk Samples; Am. J. Vet. Res. Nov. 1964. 25. 109; pp. 1658-1662.

Whittlestone et al. The Australian Journal of Dairy Technology, Dec. 1966; pp138-139.

Mijnen et al: "The Value of Cell Count, Lactose Content, PH and Conductivity of Milk for Mastitis Detection in Individual Cows"; *Netherlands Milk and Dairy Journal;* (vol. 36, 1982; pp. 65-77).

"Influence of Varying Milking Intervals On Milk Composition—A Psysiological Approach On Secretion of "Normal Milk"", J. Hamann & H. Halm, Automatic Milk—A Better Understanding, pp. 215-220.

* cited by examiner

MASTITIS DETECTION METHOD

TECHNICAL FIELD

This invention relates to a mastitis detection method.

BACKGROUND ART

Mastitis is a condition encompassing the infection and inflammation of the mammary glands in animals and humans. Reference throughout this specification will be made to the use of the present invention to detect mastitis in ruminants such as cows. However, it should be appreciated that the reference to cows is by way of example only and the present invention can also have application to the detection of mastitis in other animals and possibly humans.

Mastitis is an expensive disease, costing dairy farmers-significantly whether through lower quality milk, smaller yields plus the time and expense spent treating mastitis.

There are two main stages of mastitis.

Clinical mastitis can be detected visually through observing red and swollen mammary glands and through the production of clotted milk. Once detected, farmers divert milk from mastitic cows or teats to a waste line so that it is not collected in the main milk vats during milking and therefore will not adversely affect milk quality.

Sub-clinical mastitis cannot be detected visually through either observation of the gland or the milk produced. Because of this, farmers do not have the option of diverting milk from sub-clinical mastitic cows or teats. Yet, this milk is of poorer quality than that from non-infected cows and can thus contaminate the rest of the milk in the vat.

Further, there is a lower milk yield from cows having sub-clinical mastitis, and the real likelihood that clinical mastitis will shortly develop with its associated problems including significant damage to udder tissue.

Thus, the earlier that mastitis can be detected, particularly in the sub-clinical stage the better. With less damage to the udder, there is a longer time that the cows can produce and the milk that they produce is of greater quality.

It has been estimated that sub-clinical cases of mastitis cost the industry more than clinical mastitis in terms of financial loss (*Douglas* et al., 1997).

Currently there are a number of ways by which mastitis is detected.

One method is initial detection by the farmer of clots on the milk filter. This can indicate to the farmer that there is mastitis in the herd.

This method of detection is obviously too late to prevent contamination of the milk vat for that day. However, the farmer can be alerted to check every teat in his/her herd, either by visually assessing if there is infection and/or squirting milk from the teat onto the milking shed floor to determine if there are clots therein.

Along with late detection in terms of the ability to divert milk, this method is also labour intensive as it involves inspection of a whole herd. Another problem is that this method does not detect sub-clinical mastitis.

Another method, used to detect mastitis is somatic cell counts. This normally involves taking a sample of milk from the cow and then sending the sample to a laboratory to be tested in a specialised and expensive cell counter machine.

This test has the advantage that it is good at detecting sub-clinical mastitis, but has the disadvantage in that the test is only undertaken at intervals usually of at least one week. In New Zealand, routine somatic cell counts are undertaken daily on a bulk milk sample from the milk vat. The presence of mastitis in the herd can be detected by a sudden increase in somatic cell concentrations but the farmer is then faced with the problem of finding the infected quarter(s) in the herd.

Another method of testing for mastitis involves testing the conductivity of the milk (*Woolford* et al., 1997). A conductivity test has advantages in that it can be relatively quick to obtain results and the conductivity tester may be a handheld device or in preferred uses of this method an in-line device for use in the milking machine. In this case, mastitic milk can be detected and diverted from the main milk vat.

A further advantage of this method is that the infected cow can be detected by the milking machine at the time of milking, allowing for the cow to be treated for mastitis while still in the milking shed.

However, there are problems associated with this test. For example, the present methods of measuring conductivity give a large number of false positives and false negatives.

Further, the conductivity of milk changes during the milking process along with the fat proportion. Thus, at any one time the conductivity measure is not necessarily measuring representative samples.

Another complication is that cows on heat have a different level of conductivity in their milk than other cows.

Yet another problem is that conductivity has not been shown as being sufficiently sensitive to determine sub-clinical mastitis.

It is an object of the present invention to address the foregoing problems or at least to provide the public with a useful choice.

Further aspects and advantages of the present invention will become apparent from the ensuing description which is given by way of example only.

DISCLOSURE OF INVENTION

According to one aspect of the present invention there is provided a method for detecting mastitis in an animal, characterised by the steps of a) collecting milk from the animal, and b) assaying the milk for a substance produced in the animal in an anaerobic environment, and c) comparing the substance levels obtained with typical substance levels found in uninfected milk.

Reference throughout this specification shall now be made to the animal as being a cow, however it should be appreciated that the term animal can mean any animal, including humans and ruminants such as sheep and goats.

In preferred embodiments of the present invention the substance assayed for it lactic acid or lactate. These terms will be used interchangeably.

Reference throughout this specification shall now be made to use of the present invention by measuring the level of lactate or lactic acid in the milk of the animal being tested. This however should not be seen to be limiting.

The term 'level' can be any relevant measurement, but in preferred embodiments of the present invention, the term 'level' shall refer to the concentration of lactic acid with reference to the units of millimolar (mM).

The applicant has found in particular that L-lactic provides the most reliable indication of the existence of mastitis. Lactate milk can be present in L- or D-form. L-lactic is often the final product in the metabolism of a living organism where oxygen is limiting. D-lactic is less common in nature but is formed by some micro-organisms. In the present invention the lactate is either L-lactate or a mixture of L-lactate and D-lactate. The ratio of the two enantiomers can vary from about 1 to 100 parts L-lactate to one part D-lactate. Generally however, it appears that D-lactate only forms a significant proportion of the total at low overall lactate levels.

The applicant has found that non-infected milk from cows generally has a concentrate of L-lactate of approximately 0.1 mM and generally in the range 0.05 to 0.15 mM across a variety of breeds and cows within breeds.

In particular, the applicant has found that a concentration in the order of 0.2 mM is an indicator that sub-clinical mastitis is likely and further investigation is warranted in terms of assessing whether the teats have mastitis.

Concentrations of 0.5 mM or more provides reasonable certainty that the milk came from a mastitic teat which indicates to the farmer that the cow should be treated and the milk from the infected teats should be kept separate from the non-infected milk from the rest of the herd.

In some embodiments of the present invention, the lactate tests may be performed in combination with other tests to give greater certainty. For example, if the lactate level is testing between 0.2 mM and 0.5 mM, this may be a prompt for somatic cell counts and conductivity tests to be conducted as well to give greater certainty as to whether the infection is there.

One of the advantages of testing for lactate, it that it can be a relatively quick test and portable lactate meters or sensors are available on the market.

There is no need to send the milk away to a laboratory and wait for the results as it is possible that measurement of lactate may be conducted in line as are present conductivity methods. This means that the milk can be diverted if the lactate levels are sensed as being higher than a certain concentration (say 0.5 mM) and the cows are treated in the shed.

The applicant has found that testing for lactate gives a greater certainty in the detection of sub-clinical mastitis than conductivity and there is less variability in lactate levels during the milking process irrespective of the reproductive cycle of the cow.

The applicant has found that the detection of lactate gives a good indication of sub-clinical mastitis in addition to clinical mastitis.

Lactate can be measured in milk in a variety of ways. Some methods are based on measurement of NAD to NADH and the lactate dehydrogenase reaction. The increase of NADH is determined by means of its absorbance at 340 nm. Other methods include use of near infra-red spectroscopy to detect lactate.

BRIEF DESCRIPTION OF DRAWINGS

Further aspects of the present invention will become apparent from the ensuing description which is given by way of example only and with reference to the accompanying drawings in which.

BEST MODES FOR CARRYING OUT THE INVENTION

Figure 1:
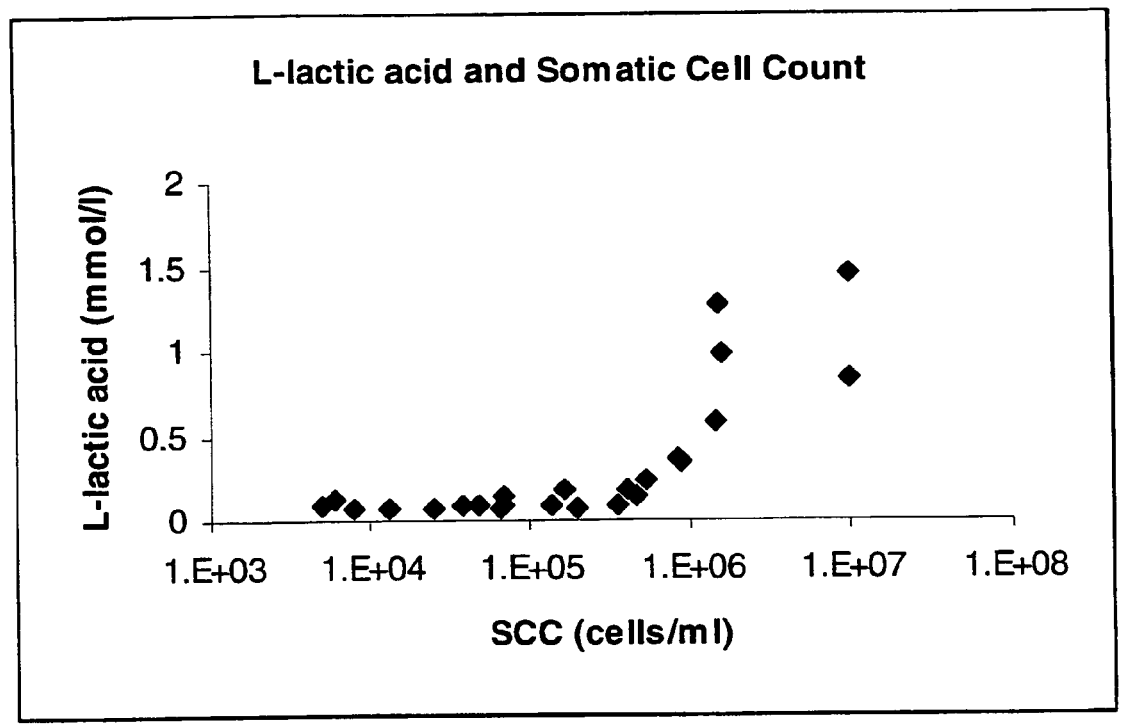
FIG. 1 is a graph of the L-lactic acid concentration measured in milk in comparison with somatic cell counts for the same milk samples.

To provide the data for FIG. 1, the following procedure was followed.

Milk samples were collected from cows known to have mastitis problems. Samples were collected from both an infected and controlled quarter. One sample was collected aseptically from the infected quarter and analysed for bacteriology.

L-lactic acid was measured in deproteinised milk using Boehringer analytical kits. The volume of reaction in the kits was reduced to one-tenth of that recommended as the assay was scaled down to a microplate format for ease of assay of multiple readings and economy of resources.

Somatic cell count was determined by using a cell counter (Fossomatic 550, Foss Electric, Hillerod, Denmark).

FIG. 1 illustrates quite clearly that the concentration in lactic acid is relatively constant until the somatic cell count reaches a level in the order of 800,000 to 1,000,000 cells per ml. Depending on the infective organism, sub-clinical mastitis can be present when somatic cell counts are above 1,000,000 cells per ml. Thus, it can be seen that the concentration of lactate can be a sensitive test to determine the presence of sub-clinical mastitis.

Figure 2:
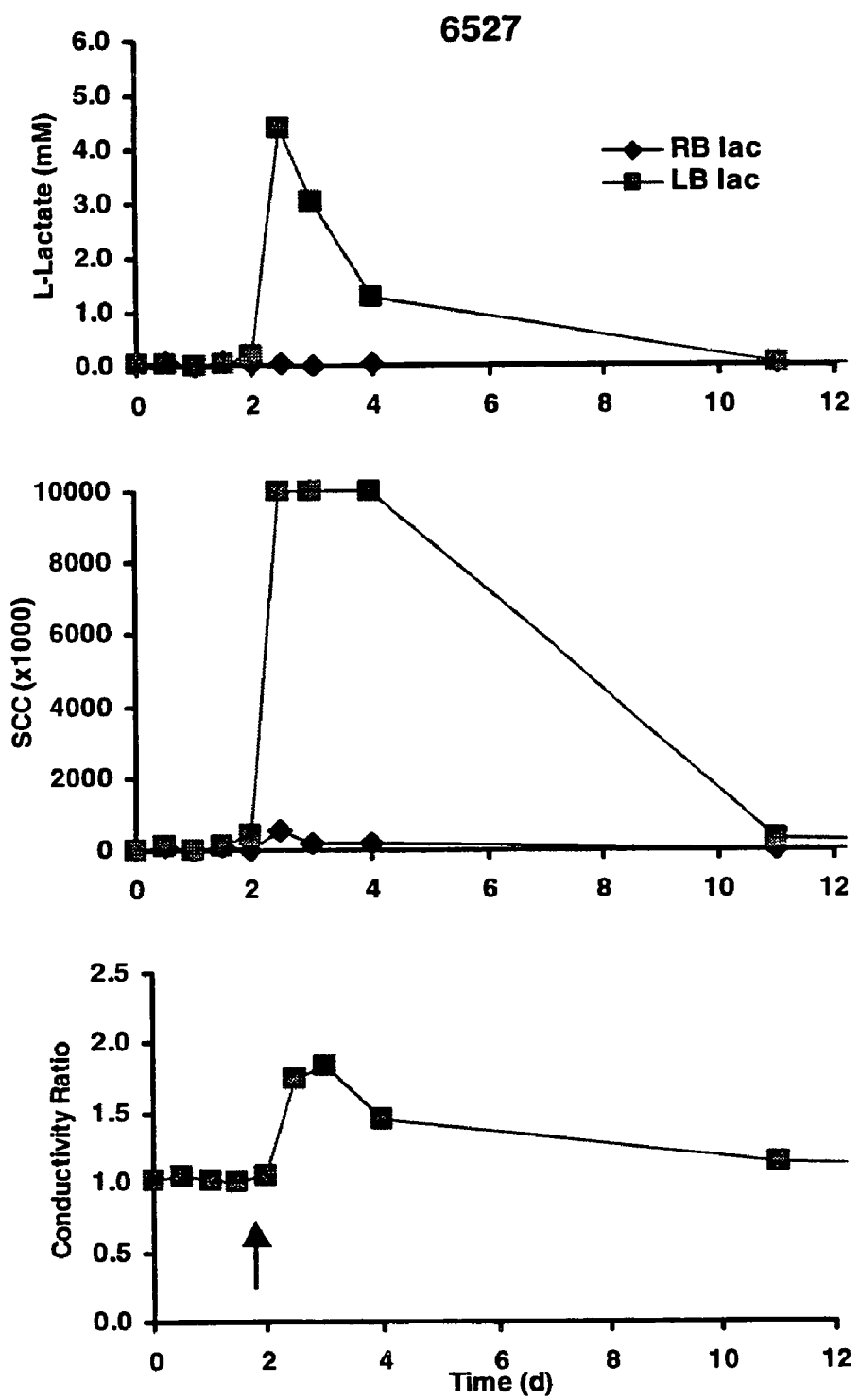
FIG. 2 is a comparison of lactic acid concentration with somatic cell count and conductivity ratio from a single cow.
Figure 3:
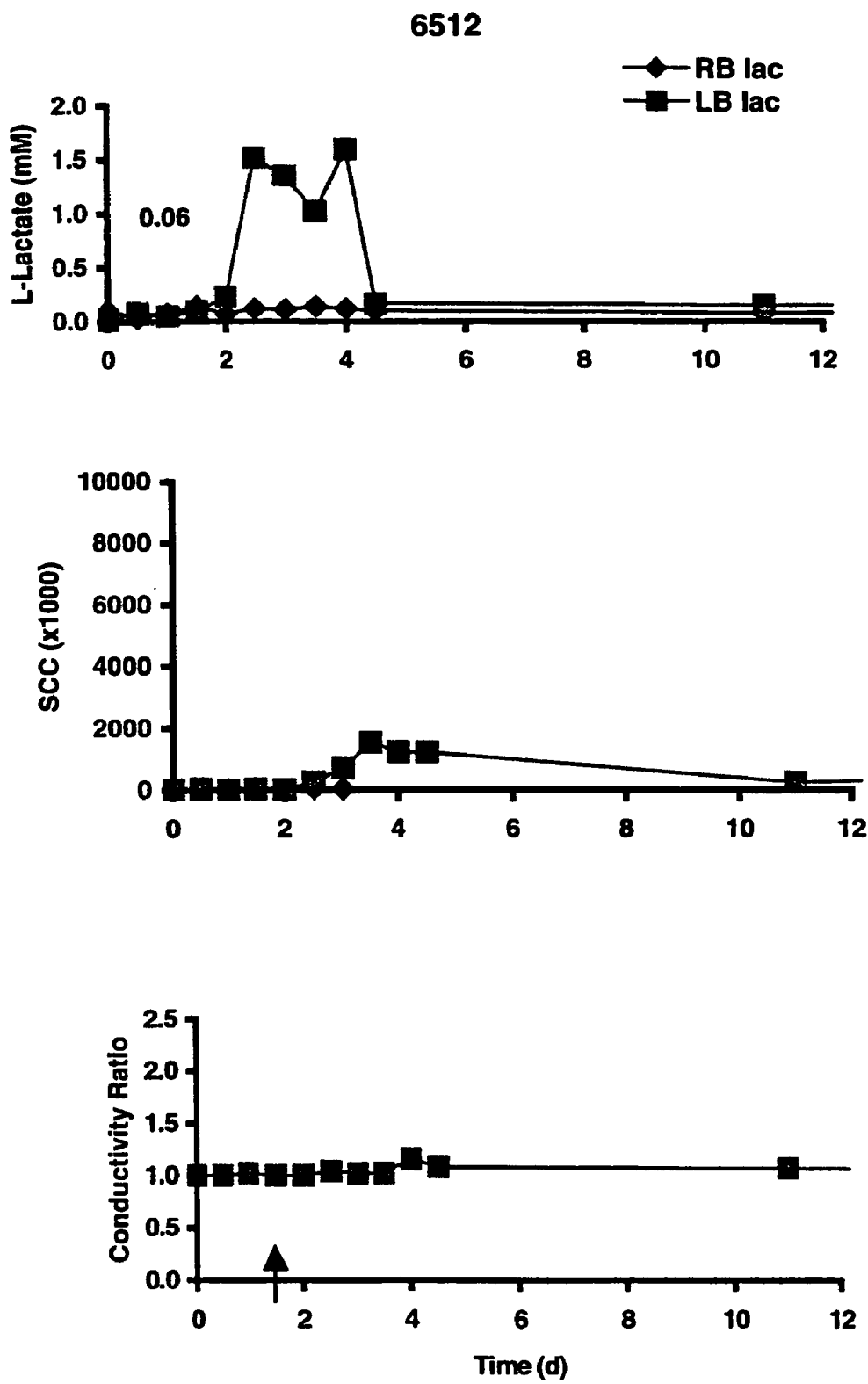
FIG. 3 shows the same comparisons as in FIG. 2, but for another cow.

FIGS. 2 and 3 results from two individual cows from a study of ten mid-lactation cows as described below.

Experimental Design

Ten, mid-lactation cows, with no recent (3–4 mths) history of mastitis infection were chosen for this trail. Cows were foremilk quarter-sampled and conductivity measured at four milkings before intramammary infusion of pathogen. Samples from the first milking were tested for the presence of bacteria and all pre-infusion samples has somatic cell concentrations (SCC) measure to ensure quarters were well clear of infection before infusion. Cows received 1000 colony-forming units (sfu's) of a mild strain of *Streptococcus uberis* into one rear quarter after an afternoon milking (t=0 h). The bacteria were administered by infusion, via the teat into the left back quarter. The right back quarter was not treated. All quarters were observed for signs of infection and conductivity measurements compared to those pre-infusion. The two rear quarters were foremilk sampled at normal milking times either until there were signs of clinical mastitis or until 72 h after infusion (t=72 h). After this milking (or appearance of clinical symptoms), infused quarters began treatment with a course of intramammary antibiotic previously shown to be potently bactericidal to the pathogen.

Milk yield was recorded throughout the experimental period and her test (composite) milk samples taken for SCC and lactate analyses.

Analyses:

Electrical conductivity was determined in fore-milk samples using a hand-held conductivity meter (Technipharm). The presence of *S. Uberis* in milk was determined as described by *Woolford* et al., 1998, J. Dairy Research 65.187–198.

Somatic cell concentrations were determined by a cell counter (Fossomatic 450, Foss Electric, Hillerod, Denmark) and L-lactate was measured in deproteinised milk using a Boehringer analytical kit. The conductivity ratio was calculated from the conductivity of the infused quarter divided by the lowest conductivity of the non-infused quarters.

Herd test (composite) milk samples were analysed for SCC and L-lactate.

Results

FIG. 2 shows typical results from an animal a showing clinical mastitis within 24 h of pathogen being infused. SCC rose to >10 million/ml after 24 h and this was accompanied by large changes in conductivity ratio. Milk lactate concentrations rose from below 0.1 mM to between 3.0 and 6.0 mM, 24 h post-infection in the infected quarters but remained unchanged in milk from the control quarters. All cows were treated with antibiotic after the 24 h milking and SCC and lactate concentrations returned to normal within a further 10–11 days.

Three cows showed no clinical signs of mastitis, although SCC and lactate concentrations were elevated. Typical data from one of these cows are shown in FIG. 3. There was little change in conductivity ratio apparent in milk from these animals. Antibiotic treatments were given at the tenth milking and recovery of SCC and lactate was sustained until day 11.

Bacteriology results demonstrated the presence of *S. Uberis* in milk samples from all cows at 16 hours post-infection.

Conclusions

From the trial where mastitis infections were induced, all cases of ensuing infections would have been detected within 24 h if a threshold lactate measurement of 0.5 mM had been used on quarter milk samples. In the tenth cow, the SCC response was mild and the change in milk lactate relatively small. In this animal, the infection appeared to be eliminated by the cow's own defences.

For composite samples, a threshold of 0.5 mM would have detected the presence of mastitis in the 6 cows showing clinical mastitis. In the remaining animals, changes in SCC and lactate were very small.

A strong relationship between milk lactate and SCC contents was shown, especially when SCC rose above 1 million cells/ml.

Additional data:

Comparison of foremilk samples taken at morning and afternoon milkings from cows that had established infections indicated that lactate concentrations were higher in samples taken in the afternoon (data not shown).

Comparison of lactate concentrations in fore-milk and milk obtained after normal milking indicated that milk lactate remained elevated throughout milking although lactate concentrations tended to be highest in fore-milk (data not shown).

Aspects of the present invention have been described by way of example only and it should be appreciated that modifications and additions may be made thereto without departing from the scope thereof as defined in the appended claims.

REFERENCES

Douglas, V. L. et al. (1997) Use of individual cow somatic cell counts, electrical conductivity, and the rapid mastitis test on individual quarters to diagnose sub-clinical mastitis in early lactation with an economic assessment for antibiotic therapy. *Proceedings of the 2<sup>nd</sup> International Conference for the Society of Dairy Cattle Veterinarians of the NZ Veterinary Association* June: 80–90.

Woolford et al. (1997) Changes in electrical conductivity and somatic cell count between milk fractions from quarters sub-clinically infected with particular mastitis pathogens. *Journal of Dairy Research* (1998) 65:187–198.

The invention claimed is:

1. A method for detecting mastitis in an animal, which comprises the steps of:
    (a) collecting milk from the animal, and
    (b) assaying the milk for L-lactate, and
    (c) comparing the L-lactate levels obtained with typical L-lactate levels found in uninfected milk, wherein a concentration of L-lactate between 0.2 mM and 0.5 mM is used as an indicator to further investigate likely presence of mastitis.

2. The method as claimed in claim 1, wherein the animal is a cow.

3. The method as claimed in claim 1, which is used in conjunction with an additional test for mastitis.

4. The method as claimed in claim 1, further comprising the step of assaying the milk with an in-line L-lactate sensor in the milking machine.

5. A method for assessing milk quality which comprises the steps of
    a. assaying the milk for L-lactate, and
    b. comparing the L-lactate levels obtained with typical L-lactate levels found in uninfected milk, wherein a concentration of L-lactate between 0.2 mM and 0.5 mM is used as an indicator to further investigate the likely presence of mastitis.

6. The method as claimed in claim 5 wherein the animal is a cow.

7. The method as claimed in claim 5 which is used in conjunction with an additional test for mastitis.

8. The method as claimed in claim 5, further comprising the step of assaying the milk with an in-line L-lactate sensor in the milking machine.

9. The method of claim 1, wherein said mastitis is sub-clinical mastitis.

10. The method of claim 1, wherein said mastitis is clinical mastitis.

11. A method for detecting mastitis in an animal, which comprises the steps of:
    (a) collecting milk from the animal, and
    (b) assaying the milk for L-lactate, and
    (c) comparing the L-lactate levels obtained with typical L-lactate levels found in uninfected milk, wherein a concentration of L-lactate greater than 0.5 mM is treated as an indicator of mastitis.

12. A method for assessing milk quality which comprises the steps of
    a. assaying the milk for L-lactate, and
    b. comparing the L-lactate levels obtained with typical L-lactate levels found in uninfected milk, wherein a concentration of L-lactate greater than 0.5 mM is treated as an indicator of mastitis.

* * * * *